United States Patent [19]

Drewes et al.

[11] Patent Number: 4,652,636
[45] Date of Patent: Mar. 24, 1987

[54] PENTENE-DIPHENYL-DIGLUCOSIDE CONTAINING COMPOUND

[75] Inventors: Siegfrid Drewes, Pietermaritzburg; Roelof W. Liebenberg, Johannesburg, both of South Africa

[73] Assignee: Roecar Holdings, Amsterdam, Netherlands

[21] Appl. No.: 729,683

[22] Filed: May 2, 1985

Related U.S. Application Data

[63] Continuation of Ser. No. 486,409, Apr. 19, 1983, abandoned.

[30] Foreign Application Priority Data

Apr. 19, 1982 [GB] United Kingdom ............... 8211294

[51] Int. Cl.$^4$ ........................................... C07H 15/203
[52] U.S. Cl. .................................................... 536/4.1
[58] Field of Search .......................... 514/25; 536/4.1

[56] References Cited

PUBLICATIONS

Pegel, "Chem. Abst.", vol. 80, 1974, p. 12672(k).
Pegel, "Chem. Abst.", vol. 80, 1974, p. 19536(c).
Holdings, "Chem. Abst.", vol. 89, 1978, p. 135842(j).
Van Staden, "Chem. Abst.", vol. 95, 1981, p. 165,595(x).

*Primary Examiner*—Johnnie R. Brown
*Attorney, Agent, or Firm*—Ladas & Parry

[57] ABSTRACT

The invention relates to the treatment and prevention of cancerous conditions by the administration of a composition including the compound of the formula:

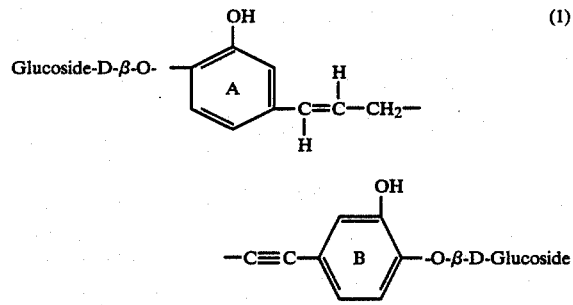

or of an aqueous, alcoholic or aqueous alcoholic or other extracts of plants of the Hypoxidaceae family and particularly the plants of the genus Hypoxis and the genus Spiloxene.

1 Claim, No Drawings

PENTENE-DIPHENYL-DIGLUCOSIDE CONTAINING COMPOUND

This is a continuation of co-pending application Ser. No. 486,409 filed on Apr. 19, 1983, now abandoned.

This invention relates to pharmacutical compositions for use in the treatment and prevention of cancerous conditions, as well as to methods for the preparation of such compositions.

PRIOR ART

Extracts of plants of the Hypoxidaceae family have been found be be active in in vivo screening tests with mouse P388 for the treatment of lymphocytic leukemia ('Distribution of Anticancer Activity in Higher Plants' A. Barclay and R. E. Purdue, Cancer Treatment Reports 1976, 60 1081-1113). For the purposes of this specification, lymphocytic leukemia is not regarded as a cancerous condition, and if it is, such condition is excluded from the scope of the invention. Extracts of the Hypoxis genus have also been used for anti-inflammatory and prostata hypertrophy treatment (U.K. patent Nos. 1595240, 1417272, 1259503.)

DEFINITIONS OF THE INVENTION

According to the invention a composition useful in preventing or treating cancerous conditions, includes the compound of Formula I below and in a preferred form, includes an aqueous, alcoholic, aqueous alcoholic, or other extract of a plant of the Hypoxidaceae family.

It is believed that all species of the Hypoxidaceae family are useful in this respect, but particularly good results have been obtained using extracts from species of the Hypoxis genus such as *Hypoxis acuminata, Hypoxis nitida, H. obtusa-nitida, H. latifolia, H. rigiduli, H. rooperi*. In particular, an ethanol extract of *H. rooperi* and *Spiloxene schlechteri* gave excellent results.

Without wishing to be restricted to a theory, it has appeared to the Applicant that the anti-cancer activity of such extract is due to the presence of the compound:

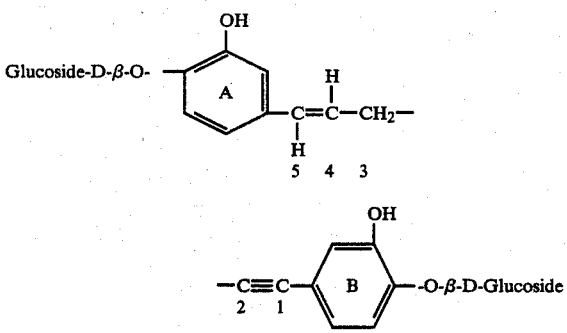

and its glycoside cogeners.

Dosages vary from individual to individual and also on the severity of the cancerous condition. However it has been found that daily dosages of from 600 mg to 2400 mg of powder obtained from extraction of plants or 300 mg to 1200 mg of compound (I) are effective As mentioned above the extraction may be carried out with water or an alcohol or a mixture thereof. The following examples illustrate the methods of extracting to the invention.

EXAMPLE 1

Freshly pulped corms of *Hypoxis rooperi* (10 kg) were extracted with ethanol (25 l) at room temperature for 48 hours. Filtration, and concentration in vacuo, followed by freeze-drying gave a brown powder (729 g). This crude material (10) was separated by preparative HPLC using a reverse phase column (PrepPAK-500/$C_{18}$) with MeOH-$H_2O$ (50:50) as solvent and gave 6.9 g of an enriched fraction. Final separation took place by separating 10 g portions of this material on a Si gel 60 column (230–400 mesh 45 mm×600 mm) with butan-2-ol-$C_6H_6$-$H_2O$-MeOH (4:3:2:1) as solvent. Typically a 10 g fraction yielded 7.9 g (40% from the fresh corms) of crystalline (I) from butan-2-ol, m.p. 147°–148° C., $[\alpha]^{20}$, −110° ($\lambda$, 0.45 in methanol). (Found: C, 54.18, H, 6.01, Calc for $C_{29}H_{34}O_{14}.2H_2O$: C. 54.20; H, 5.96; $H_2O$ 5.61%); $\nu_{max}$ (KBr): 3150–3500 (H bonded OH) cm$^{-1}$ $\lambda$max (MeOH): 247, 257 and 287 nm; $\delta(CD_3OD)$, 3.10–4.05 (14H, m, 2 protons on C-3 and 12 glucosylprotons), 4.75 (2H, m, 2 protons on C-1), 6.06 (H, dt, J=15.0 and J=5.0 Hz; proton on C-4), 6.53 (1H, d, J=15 Hz, proton on C-5), 6.65–6.90 (4H, m, Arom H), 7.07 (2H, d, Arom H).

EXAMPLE 2

The following further extractions were carried out for purposes of evaluation of the best methods and conditions of extraction.

(a) Grated corms (10 kg) of *Hypoxis rooperi* were air dried and the product (2.95 kg) was extracted for 1 hour with boiling water (20 l). Spray drying of this extract provided a partially water soluble light brown powder (550 g), which contained 20% of Compound (I).

(b) Gums obtained by centrifuging off the solid material from macerated corms (10 kg) of *H. rooperi* were diluted with cold water (1.5 l, 5° C.) and the centrifugate (4 l) was spray dried to yield a partially water soluble light cream coloured powder (900 g) which contained 30% of Compound (I).

(c) Pulped corms of *Hypoxis obtusa-nitida* (10 kg) were extracted with water (15 l, 25° C.) with occasional stirring for 6 hours. The filtered extract (12.78 l) was freeze dried to yield a partially water soluble light brown powder (757 g) which contained 35% of Compound I. The residual wet pulp (10.8 kg) was extracted with boiling absolute ethanol (10.8 l) for 20 minutes. The filtered extract was concentrated under vacuum to remove most of the alcohol, diluted with water (1 liter), and then freeze dried to provide an almost completely water soluble light brown powder (361 g) which contained 43% of Compound (I).

(d) Pulped corms of *H. obtusa-nitida* (10 kg) were extracted with boiling water (15 l) for 5 minutes. The filtrate (10.4 l) was freeze dried to provide a partially water soluble light brown powder (742 g) which contained 37% of Compound (I).

(e) Pulped corms of *H. obtusa-nitida* (10 kg) were extracted with absolute ethanol (25 l, 25° C.) for 66 hours with continuous stirring. The filtrate (23 l) was concentrated under vacuum to remove most of the alcohol, diluted with water (1 liter) and then freeze dried to provide a water soluble dark brown powder (i) (630 g) which contained 45% of Compound (I). The residual moist pulp (8.05 kg) was extracted with boiling absolute ethanol (20 l). The filtrate treated as described above was freeze dried to provide an almost completely water soluble dark brown powder (ii) (99 g) which contained 42% of Compound (I).

(f) Thinly sliced corms of *H. obtusa-obtusa* ((10 kg) were freeze dried to provide dried material (3.086 kg). This dried material was milled and a portion (300 g) was extracted with boiling 50% aqueous ethanol (5 l) for 5 minutes. The filtrate was treated as described above and freeze dried to provide a water soluble light cream powder (116 g) which contained 35% of Compound (I).

(g) Pulped corms of young *H. obtusa-nitida* were extracted with boiling water (5 l) for 5 minutes. The filtrate on freeze drying provided a partially water soluble light brown powder (54 g) which contained 32% of Compound (I).

(h) An extraction on young *H. obtusa-nitida* corms as described under (g) above, but prolonging the boiling process to 20 minutes, resulted in a relatively insoluble dark brown powder (82.3 g) which contained 27% of Compound (I).

(i) Fresh *Hypoxis acuminata* corms are pulped directly into ethanol at room temperature (1.5 kg corms per 2 l ethanol). After stirring the pulp for 1 hour it is filtered. The filtrate is evaporated under vacuum (30 Kpa) at elevated temperatures (70°–85° C.). The obtained residue is freeze dried to provide a yellow-brown product in 7–10% yield from the fresh corms. The content of I on this extract varies between 42–57%. These yields depend on seasonal variations.

(j) Fresh *Hypoxis acuminata* corms are sliced directly into liquid nitrogen. The frozen slices are freeze-dried and milled to a fine powder. This powder is then extracted with aqueous alcohol (1 part water to 2 parts of ethanol or methanol) using 6 l of the solution per 1 kg of plant powder. After 30 minutes stirring the mixture is filtered. Evaporation of the solution from the filtrate as described in example 2i provides a yellowish-brown product in 9–12% from the original fresh corms. The content of I of this extract varies between 49–56%. Yields depend on seasonal variations.

k. Pulped corms of *Spiloxene schlechteri* on treatment with aqueous ethanol provided an extract which contained a substantial amount of Compound (I).

The above evaluations were obtained by comparative thin layer chromatography and HPLC analysis.

EXAMPLE 3

In order to demonstrate the activities of the extracts of the invention, cytotoxicity tests were carried out on M(52)B cell culture systems in vitro.

Mouse Sarkoma cells M(52)B were cultured as monolayers in M.E.M. with 106 foetal calf serum. After confluency was achieved (usually within 3–4 days depending on the number of cells added per bottle) the cells were trypsinized. Once loose the cell suspension was treated with M.E.M. containing 10% foetal calf serum in order to inactivate the trypsin.

An arbitrary volume of the suspension was then transferred to fresh nutrient solution rendering a final volume of 5 cm$^3$.

The test material was added at different concentrations to either the freshly prepared cell suspension or to the 24 hour developed cell culture in which the monolayer had a confluency of at lease 40 to 50%

All procedures were carried out under sterile conditions in a laminar flow chamber.

RESULTS

The addition of adequate amounts of the test material resulted in cell death within 24 hours. In other words the transferred cells failed to attach themselves on the bottom surface of the tissue culture flask, while the untreated control cells formed a confluent monolayer within 48–72 hours.

When less than adequate amounts of the test material were added some regeneration of the cells became apparent in the culture flasks over the first 24 hours. However, in these cases it took more than 10 days to achieve a 40–60% confluency, indicating that the larger proportion of the transferred cells had been completely destroyed.

TABLE 1

Percentage confluency due to *H. obtusa-nitida* (extracts ex example 2e(i)

| Agent | Dose mg/ml | Observation period in days confluency in % | | | | |
|---|---|---|---|---|---|---|
| | | 1 | 3 | 6 | 10 | 14 Days |
| Control | nil | 60 | 90 | split at 4 days | — | — |
| Extract from example 2e(i) | 0.4 | few growing cells | ±5 | ±10 | ±40 | 30–80 |
| | 0.8 | (?) | n/g | n/g | n/g | + |
| | 1.6 | n/g | n/g | n/g | n/g | n/g |
| | 2.4 | n/g | n/g | n/g | n/g | n/g | n/g No observed growth, with only isolated cells attached to the bottom surface of tissue culture flask.

The extracts of the invention may be administered as such but preferably in the form of their spray-dried or freeze dried powders, in which case they may be provided in the form of tablets, capsules, dragees, creams, powders, ointments and any other usual form of medicament. The recognised additives may also be present to improve tabletting, capsuling and the like. Dosage units may contain from approximately 100 mg to approximately 50 mg of extract per unit dose, and the rate of administration is 1 to 3 units, 3 times per day.

EXAMPLE 4a

Acute toxicity evaluation of the Hypoxis extract

Toxicity tests were carried out with solutions prepared from extracts as described in example 2e(i) using groups of mice (equal numbers of males and females).

The weight of the animals ranged between 22 and 30 g. The follow-up observation period extended over 7 days following the administation of a single dose per animal.

The prepared solutions were filtered through Millex filter membranes (0.45 mm) before they were administered intravenously in order to remove any particles which may complicate the interpretation of the results and to obtain a sterile solution.

For the oral or intraperitoneal route the solutions were administered as prepared, i.e. without prior filtration.

The results are presented in Table 2.

TABLE 2

Cumulative percentage mortality due to *H. obtusa-nitida* extract (example 2e(i))

| Dose mg/kg | Route of admin | Cumulative % mortality Days | | | | |
|---|---|---|---|---|---|---|
| | | 1 | 2 | 3 | 5 | 7 |
| 500 | P.O | 0 | 0 | 0 | 0 | 0 |
| 1000 | P.O | 0 | 0 | 0 | 0 | 0 |
| 2000 | P.O | 0 | 0 | 0 | 0 | 0 |
| 500 | I.P | 0 | 0 | 0 | 0 | 0 |
| 1000 | I.P | 10 | 20 | 20 | 20 | 20 |
| 2000 | I.P | 60 | 75 | 80 | 80 | 80 |
| 500 | I.V | 0 | 0 | 0 | 0 | 0 |
| 1000 | I.V | 20 | 25 | 25 | 25 | 25 |
| 2000 | I.V | 80 | 100 | — | — | — |

EXAMPLE 4b

Acute toxicity evaluation of (I)

Solutions of (I) in distilled water were prepared with the required concentration. Administered volumes were kept constant at the rate of 10 cm$^3$ per kg. In each case equal numbers of males and females were treated with a single dose. All animals were observed over 7 days for signs of toxic and/or pharmaco-dynamic effects.

A necropsy was performed on all surviving animals. Results are presented in the Table.

TABLE 3

Acute toxicity evalution of (I) on oral, intraperitoneal, and intravenous administration.

| Species | Administration Mode | Dose mg/kg | Mortality (Range %) | Remarks |
|---|---|---|---|---|
| Mouse | Oral | 1000 | 0/20 | No macroscopic lesions were found in any animal |
| | | 2000 | 0/20 | |
| | | 4000 | 0/20 | |
| Mouse | Intraperitoneal | 250 | 0/10 | Following administration all animals exhibited signs of discomfort which increased in degree with increasing doses |
| | | 500 | 0/20 | |
| | | 1000 | 5/30 (10–30) | |
| | | 2000 | 27/30 (80–100) | |
| Rabbits | Intravenous | 50 | 0/2 | No visible effects were observed and no macropscopic lesions were found in these animals. No thrombophlebitis was found at the injection site. |
| | | 100 | 0/2 | |

Conclusions

It appears that (I) exhibits a low degree of direct toxic effects. No macroscopic lesions were observed on necropsy of the surviving animals.

EXAMPLE 4c

Foetotoxic-Teratogenic effect of (I)

Two groups of six fully impregnated mice (Swiss Webster offspring) were treated orally with aqueous solutions of (I) once per day (10 ml/kg) starting day 1 through to day 8 of the gestation period. On day 20 of the pregnancies the mice were lightly anaethetised with diethyl ether and the uterus exposed by caesarian section. The total number of implantation sites were counted. All foeti were removed and examined for
  (a) number alive and
  (b) macroscopic gross anatomical abnormalities of limbs and head.

The results were compared to a control group and are presented in Table 4.

TABLE 4

Effects of orally administered (I) on pregnant mouse foeti

| GROUP | CONTROL H$_2$O only | COMPOUND I 20 mg/kg | COMPOUND I 100 mg/kg |
|---|---|---|---|
| No of animals | 6 | 6 | 6 |
| No of implantation sites | 56 | 58 | 58 |
| No of foeti | 52 | 52 | 49 |
| No of live foeti | 51 | 50 | 45 |
| No of malformations | 1 (?) | 0 | 3 (2?) |

EXAMPLE 4(d)

"In vitro" cytostatic cytotoxic effects with *Hypoxis rooperi* extracts (example 2(e)(i)) and Compound I Four different cell culture types were used:
  i. Mouse sarcoma—Ms 52 B
  ii. Mouse melacoma—Mel B1–6
  iii. Heha 229.
  iv. Human foetal foreskin fibroblasts—HFSF (non-malignant)

Procedure: Trypsinized cells were harvested into MEM and suitably diluted to supply about 2×10$^5$ cells per cm$^3$. A culture flask containing 4,5 cm$^3$ of culture medium was seeded with 0.5 cm$^3$ of the prepared cell suspension. This cell culture was then incubated at 37° C. for 24 hours before the test substances dissolved in 0.5 cm$^3$ of the culture medium were added. All cultures were grown until an apparent 100% was achieved in the control flasks. In all cases presented in TABLE 5 cell growth was retarded considerably and growth regression was observed for MS 52 B. Mel B1–6 and Heha 229 cell cultures.

TABLE 5

| Incubation temp: 37° C. | | | | | | | | |
|---|---|---|---|---|---|---|---|---|
| Cell culture type | MS 52 B | | Mel B1 - 6 | | Heha 229 | | HFSF | |
| test material | Ext. | I | Ext. | I | Ext. | I | Ext. | I |
| amounts added in ng | 80 | 40 | 80 | 40 | 80 | 40 | 100 | 40 |
| Hours: 24 | 50 | 40 | 40 | 40 | 50 | 50 | 40 | 40 |
| 48 | 40 | 20 | 40 | 30 | 50 | 60 | 60 | 50 |
| 72 | 20 | 20 | 20 | 40 | 40 | 50 | 75 | 50 |
| 96 | 20 | 20 | 5 | 40 | 20 | 30 | 60 | 40 |
| 120 | — | — | — | 30 | — | — | — | — |

In all cases controls had reached 100% confluency by 96 hours.
Ext. = *Hypoxis rooperi* extract as prepared in example 2e(i)
I = pure Compound I as described in example 1.

Despite the small number of animals tested it seems unlikely that at the doses administered (I) exhibits teratogenic effects. There were no indications of abnormally reduced growth rate of the foeti in any of the treated groups. No adverse effects were detected in the treated mother animals.

We claim:
1. A compound of the formula

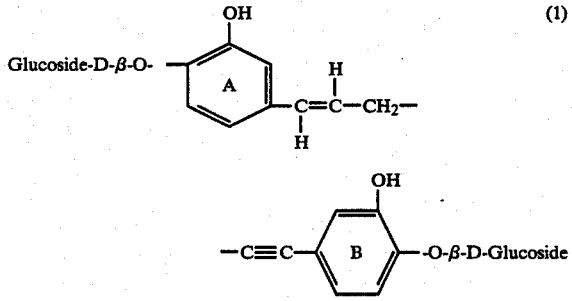

and its pharmaceutically acceptable salts.

* * * * *